United States Patent
Bouvier

(10) Patent No.: US 10,368,816 B2
(45) Date of Patent: Aug. 6, 2019

(54) MOBILE MEDICAL IMAGING ROBOT

(71) Applicant: GENERAL ELECTRIC COMPANY, Schenectady, NY (US)

(72) Inventor: Bernard Bouvier, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 552 days.

(21) Appl. No.: 15/179,937

(22) Filed: Jun. 10, 2016

(65) Prior Publication Data

US 2017/0020468 A1    Jan. 26, 2017

Related U.S. Application Data

(63) Continuation of application No. PCT/IB2013/002948, filed on Dec. 12, 2013.

(51) Int. Cl.
*A61B 6/00* (2006.01)
*A61B 6/10* (2006.01)

(52) U.S. Cl.
CPC .............. *A61B 6/4405* (2013.01); *A61B 6/10* (2013.01); *A61B 6/4441* (2013.01); *A61B 6/4464* (2013.01); *A61B 6/46* (2013.01)

(58) Field of Classification Search
CPC ....... A61B 6/10; A61B 6/4441; A61B 6/4405; A61B 6/46; A61B 6/4464
See application file for complete search history.

(56) References Cited

U.S. PATENT DOCUMENTS

| | | | |
|---|---|---|---|
| 6,131,690 A | 10/2000 | Galando et al. | |
| 2006/0104416 A1 | 5/2006 | Kump et al. | |
| 2006/0285644 A1* | 12/2006 | Camus | A61B 6/102 378/117 |
| 2008/0056451 A1* | 3/2008 | Gotoh | A61B 6/4441 378/197 |
| 2009/0310753 A1* | 12/2009 | Halsmer | A61B 6/4405 378/198 |
| 2012/0321050 A1 | 12/2012 | Bouvier et al. | |
| 2013/0003939 A1 | 1/2013 | Bouvier et al. | |

FOREIGN PATENT DOCUMENTS

| | | | | |
|---|---|---|---|---|
| EP | 2502564 A1 * | 9/2012 | .......... | A61B 6/4405 |
| WO | WO-2011067648 A1 * | 6/2011 | .......... | A61B 6/4405 |

OTHER PUBLICATIONS

International Search Report and Written Opinion for PCT/IB2013/002948, dated Aug. 19, 2014, 11 pages.

* cited by examiner

*Primary Examiner* — Chih-Cheng Kao
(74) *Attorney, Agent, or Firm* — Fletcher Yoder, P.C.

(57) ABSTRACT

A mobile medical imaging robot is disclosed. The robot comprises a medical imaging device, and a vehicle configured to carry the medical imaging device. The vehicle is motorized so as to move on a surface, such the floor of an examination room. The robot further comprises a cable designed to link said vehicle to a wall of a room, such as a medical examination room. In at least one non-limiting embodiment, motorized robot movements along the surface are controlled manually by a user.

17 Claims, 4 Drawing Sheets

MOBILE MEDICAL IMAGING ROBOT

CROSS-REFERENCE TO RELATED APPLICATIONS

This application is a continuation of co-pending International (PCT) Application No. PCT/IB2013/002948, filed Dec. 12, 2013, the contents of which are incorporated by reference herein.

BACKGROUND

This disclosure relates to mobile medical imaging robots, and to medical operating methods using such mobile medical imaging robots.

These mobile medical imaging robots usually comprise a medical imaging device supported by a vehicle, this vehicle being motorized or not. Most often, mobile medical imaging robots are free, their moving magnitude is not limited as it would be if they were for instance cable linked, that is to say linked to the structure, for example to the wall of an examination room, with a cable.

When the mobile medical imaging robots are free, they can move freely and the driving of their move is quite simple and easy, but their alimentation in power and data, for example wireless, may become more complex.

On the contrary, when the mobile medical imaging robots are cable linked to a wall, their moving magnitude is limited and causing an excessive moving magnitude may endanger the cable and or the cable connections, while at the same time the presence of permanent cable connections makes easier transfer, whether of power or data. Especially providing high alimentation power to provide high image quality during a long time will be much easier with a medical imaging robot cable linked to a wall of the examination room.

However, with cable linked mobile medical imaging robots, out of security reasons, all the more important in medical environment, moving as well as moving driving are made fully automatic, the user command being limited to a simple click asking to remove and park the robot or to bring the robot closer to an examination table, both positions being predetermined, and the traveling paths in between being predetermined too. Automatism failure is less frequent than human failure.

According to a prior art, for example described in patent applications FR 2953119 or FR 2945524, it is known a mobile medical imaging robot managed by a complete navigation system which ensures a complete security of all moves of this mobile medical imaging robot, driving of moving motorized robot being automated, but which is relatively expensive.

SUMMARY

The exemplary non-limiting embodiments described herein are configured to alleviate the above mentioned drawbacks.

More particularly, the exemplary non-limiting embodiments described herein and all combinations thereof aim to provide for a mobile medical imaging robot which is cheaper than in the prior art. Providing a manual driving of the motorized moving of the robot allows for such simplification which lowers costs. However, this is performed at the price of lowering the security level of the robot moving control, which still remains sufficient.

Then, according to exemplary non-limiting embodiments, adding some security sensors to this motorized moving manually driving restores a high level of security with respect to robot moving control, with limited additional expenses. All in all, this more manual robot with at least an added security sensor, provides for a comparable level of security with respect to robot moving control, with the benefit of a reduced complexity and of a reduced cost.

In one non-limiting exemplary aspect, a mobile medical imaging robot is described comprising: a medical imaging device; a motorized vehicle comprising at least one motor and configured to carry and move the medical imaging device along a surface; and a cable configured to link the vehicle to the surface or a wall extending from the surface, wherein the motorized vehicle are driven manually by a user.

The wall or surface may be a surface or a vertical wall of an examination room. The surface or wall may be a partition or may be a horizontal wall, like a floor or a ceiling. An examination room is a room where patients can be examined, usually on a patient table, this examination room being in a building, often in a hospital or in a clinic. This cable link is preferably a permanent link, at the vehicle side as well as at the examination room wall side, so a link that cannot be cancelled by a simple unplug, but on the contrary would need a real disassembly.

In at least one exemplary non-limiting embodiment, a mobile medical imaging robot is disclosed, wherein the robot includes a cable linked to an examination room, wherein the robot's movements along a surface, for example, on a floor of an examination room are motorized and wherein said motorized moving is driven manually by a user. In some such embodiments, the robot is cable linked to any wall of this examination room, including floor or ceiling or partition.

A complementary advantage is achieved with a medical operating method alternating, in a same examination room, either bringing closer, to a patient table, a mobile medical imaging robot according to any exemplary non-limiting embodiments described herein, for one or more interventional performances, or removing, from a patient table, said mobile medical imaging robot according to any exemplary non-limiting embodiments described herein, for one or more surgical performances.

At least one exemplary non-limiting embodiment comprises one or more of the following features, which can be taken separately or together, either in partial combination or in full combination. Preferred embodiments may be combined with any of preceding exemplary non-limiting embodiments.

In at least one exemplary non-limiting embodiment, said motorized moving can only be driven manually by a user. That way, the driving of the motorized moving being always purely manual, the system managing the moving of the robot may become very simple.

In at least one exemplary non-limiting embodiment, said robot comprises a human machine interface, preferably tactile, more preferably a joystick, adapted to perform said manual driving. Again, this human machine interface is very simple, even if it may be considered as less ergonomic than vocal command for example, and it is more secure.

In at least one exemplary non-limiting embodiment, said human machine interface is located on said vehicle, preferably at a height ranging from 0.80 m to 1.50 m. That way, the user will drive the moving robot while simultaneously walk beside the moving robot.

In In at least one exemplary non-limiting embodiment, said human machine interface is power assisted. This type of human machine saves physical effort of the user, all the more interesting when the robot is quite heavy.

In at least one exemplary non-limiting embodiment, said human machine interface transmits any planar user move, preferably any translation or rotation or combination thereof, to said vehicle so that said vehicle performs corresponding move. This makes easier the driving for the user which can directly make the robot move exactly the way he wants.

In at least one exemplary non-limiting embodiment, only a limited number of types of moves can be performed by said vehicle, wherein among said limited number of types of moves, preferably there is a rotation around a vertical axis containing the isocenter of said medical device and/or two translations orthogonal to each other. Advantageously, among said limited number of types of moves, there only are a rotation around a vertical axis containing the isocenter of said medical device and two translations orthogonal to each other. Although this is less practical for the user who is allowed only a limited type of moves, this makes the system managing the move of the robot, which is integrated in the robot, again simpler.

In at least one exemplary non-limiting embodiment, at least power for said motorized vehicle is transmitted on said cable, and on said cable is also preferably transmitted power for said medical device and/or cooling for said medical device and/or video data from said medical device. Since a cable is already present to transmit power to the robot, which allows for a better image quality which can be maintained longer, it is also useful to use this already present cable to transmit other fluids or data too, especially cooling fluids which would otherwise need a dedicated cable or added complexity to be transmitted.

In at least one exemplary non-limiting embodiment, said cable is flexible, and said cable is preferably disposed within and surrounded by a flexible chain. A flexible cable allows for a broader scope of moves of the robot without endangering the connections of the cable. A flexible chain is simultaneously a flexible element and a robust element that would be a first level of protection for the connections of the cable, if the moving amplitude of the robot were to become excessive.

In at least one exemplary non-limiting embodiment, said cable is permanently fixed to said vehicle, and wherein said cable is preferably permanently fixed to said examination room wall once said robot is installed in said examination room. This is a situation where the robot is permanently fixed to the examination room, where the moves are the more limited both in direction and in magnitude, where one would naturally think of automatically driven moves. However, still manually driving the motorized moving of the robot allows for a simpler robot and thereby for a less expensive robot.

In at least one exemplary non-limiting embodiment, said robot comprises at least one security sensor structured to detect excessive cable move, and preferably to mechanically detect excessive cable move. Because of the great liberty given to user in driving the motorized moving of the robot, out of security reasons, a sensor, especially a robust mechanical sensor, will detect and will react, without risk or with reduced risk of failure, any move presenting an excessive magnitude which could otherwise endanger the connections of the cable, whether its connection to the robot or its connection to the wall of the examination room.

In at least one exemplary non-limiting embodiment, said robot comprises a cable security system adapted to detect excessive cable tension so as to stop further move of said vehicle leading to still higher cable tension, said cable security system preferably comprising a sensor structured to mechanically detect excessive cable tension. Indeed, an excessive cable tension could endanger the cable itself as well as the connections of the cable.

In at least one exemplary non-limiting embodiment, said robot comprises a rotation security system adapted to detect excessive vehicle rotation so as stop further vehicle rotation in the same direction, a threshold of said excessive vehicle rotation being preferably at most one full turn, said rotation security system preferably comprising a sensor structured to mechanically detect excessive vehicle rotation. Indeed, an excessive vehicle rotation, in the same direction, could cause a cable entanglement which could result in endangering the cable itself as well as the connections of the cable. This threshold of said excessive vehicle rotation may be more preferably at most half a turn.

In at least one exemplary non-limiting embodiment, said medical device is a C-arm, preferably an X-ray C-arm. This type of medical device needs to be moved from time to time, since it may be needed in some situations and not be needed in other situations, while remaining permanently fixed to a wall of an examination room.

In at least one exemplary non-limiting embodiment, said medical robot weight is above 600 kg, preferably above 800 kg. Since this robot is quite heavy, some kind of motorization is very interesting, while keeping the driving very simple, for instance fully manual, is interesting too, in order to keep the costs at a reasonable or cheaper level than fully automatized systems. In the prior art, heavy systems either don't move or they are fully automatized, moving and driving of the moving, user input being often limited to clicking a button to move the robot between two predetermined positions with predetermined traveling in between too.

In at least one exemplary non-limiting embodiment, a mobile medical imaging robot comprises: a medical imaging device; a motorized vehicle comprising at least one motor and configured to carry and move the medical imaging device along a surface; and a cable configured to link the vehicle to a surface; and at least one movement monitoring system comprising at least one sensor, said movement monitoring system configured to prevent any movement beyond a corresponding acceptable movement threshold, wherein the medical imaging device, under user control, is configured to move away from an examination table to allow access to a patient, and to move toward and about the examination table to a desirable location for taking images of the patient corresponding to an area of interest.

In some such embodiment, the mobile medical imaging robot further comprising a cable security system configured to detect when cable tension exceeds a predetermined acceptable value and prevent further movement of the motorized vehicle leading to still higher cable tension, wherein the cable is flexible and is disposed within a flexible chain.

Further features and advantages of the exemplary non-limiting embodiments described herein will appear from the following description of, with reference to the accompanying drawings listed hereunder.

DETAILED DESCRIPTION

Figure 1:
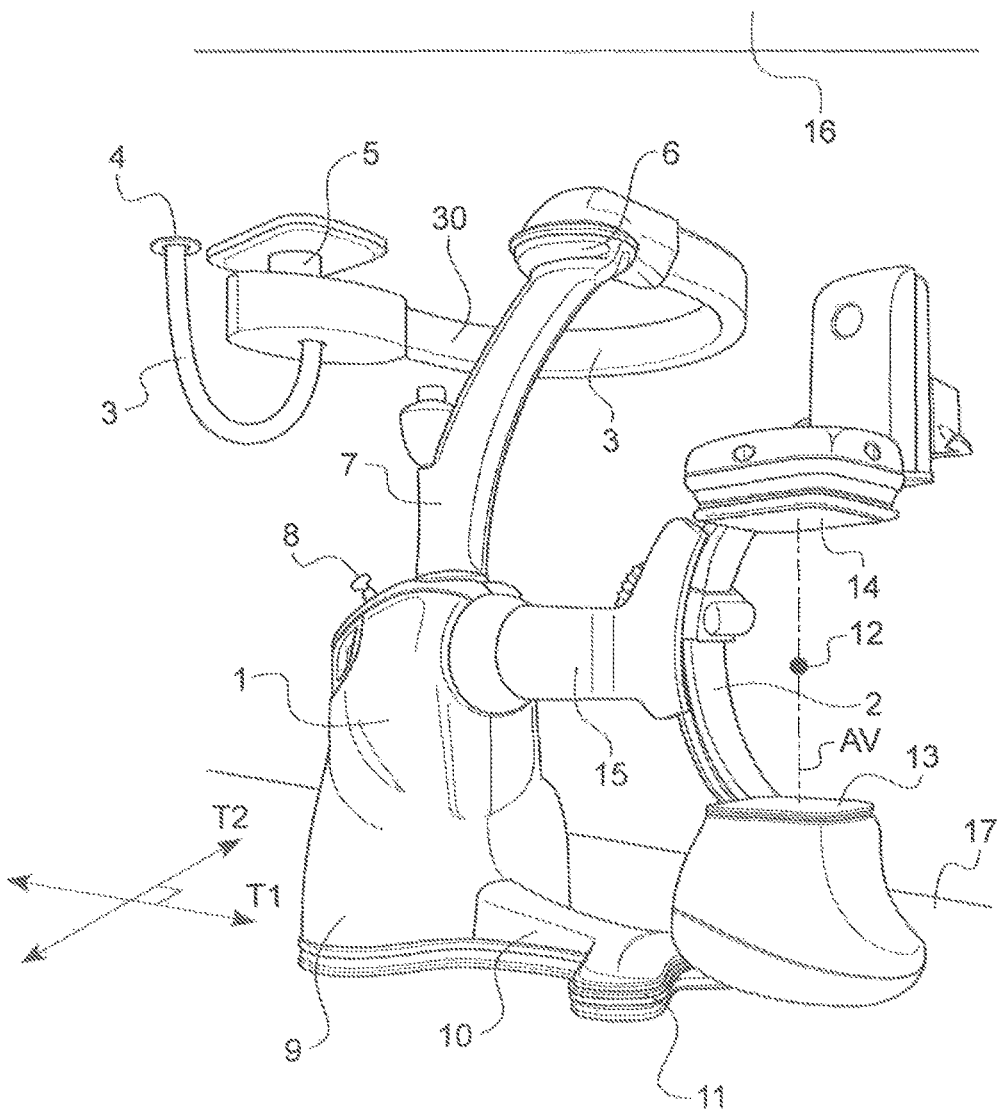
FIG. 1 shows an example of a mobile medical imaging robot according to at least one exemplary non-limiting embodiment.

FIG. 1 shows an example of a mobile medical imaging robot according to at least one exemplary non-limiting embodiment. The mobile medical imaging robot comprises a vehicle 1 supporting a medical imaging device 2 which is a C-arm. The vehicle 1 is mobile on a floor 17 of an examination room while being linked to the ceiling 16 of this examination room by a cable 3.

The C-arm 2 is held on the vehicle 1 by a horizontal arm 15. The C-arm 2 can glide in the horizontal arm 15, following the C shape, which horizontal arm 15 can also rotate around a horizontal axis. The C-arm 2 comprises a source 13 of emitted signal which is an X-ray tube and a detector 14 which detects X-ray emitted radiation. Source 13 and detector 14 are located at respective ends of the C-arm 2.

The vehicle 1 is supported by motorized wheels 9, preferably two of them, and by free wheels 11, preferably two of them. Motorized wheels 9 and free wheels 11 are linked by a linking element 10. Here, motorized wheels 9 and free wheels 11 are not directly visible because they are hidden under the cover of vehicle 1.

A humane machine interface 8 which is a joystick is located on the cover of the vehicle 11. This joystick 8 is located sufficiently high to be manipulated by a user who is simultaneously walking by the moving robot.

On the top of the vehicle 1, there is a mast 7. At upper end of the mast 7, there is a saucer 6. The cable 3 goes into the mast 7 through the saucer 6. The cable chain 30 surrounding the cable 3 is connected to the saucer 6 at one end. The saucer 6 allows for a vertical rotation, around the mast 7, of the portion of the cable 3 being outside this mast 7.

The cable 3 goes by a pivot 5 before going through a cable guide 4 to be connected to the ceiling 16. The cable chain 30 surrounding the cable 3 is connected to the pivot 5 at the other end. The pivot 5, which allows one end of the cable chain 30 to rotate vertically around it, is fixed to the ceiling 16.

The vehicle 1 may preferably move according to only three predetermined types of move, all commanded by user through joystick 8. The vehicle 1 may translate along horizontal axis T1 which is the longitudinal axis of the vehicle 1 linking motorized wheels 9 to free wheels 11. Free wheels 11 can freely rotate around a vertical axis too in order to be oriented in any horizontal direction. The vehicle 1 may translate along horizontal axis T2 which is orthogonal to horizontal axis T1. The vehicle 1 may also rotate around a vertical axis AV which contains the isocenter 12 of the C-arm 2. The isocenter 12 of the C-arm 2 is the point around which the C-arm may be rotated when taking images of a patient lying on an examination table.

Figure 2:
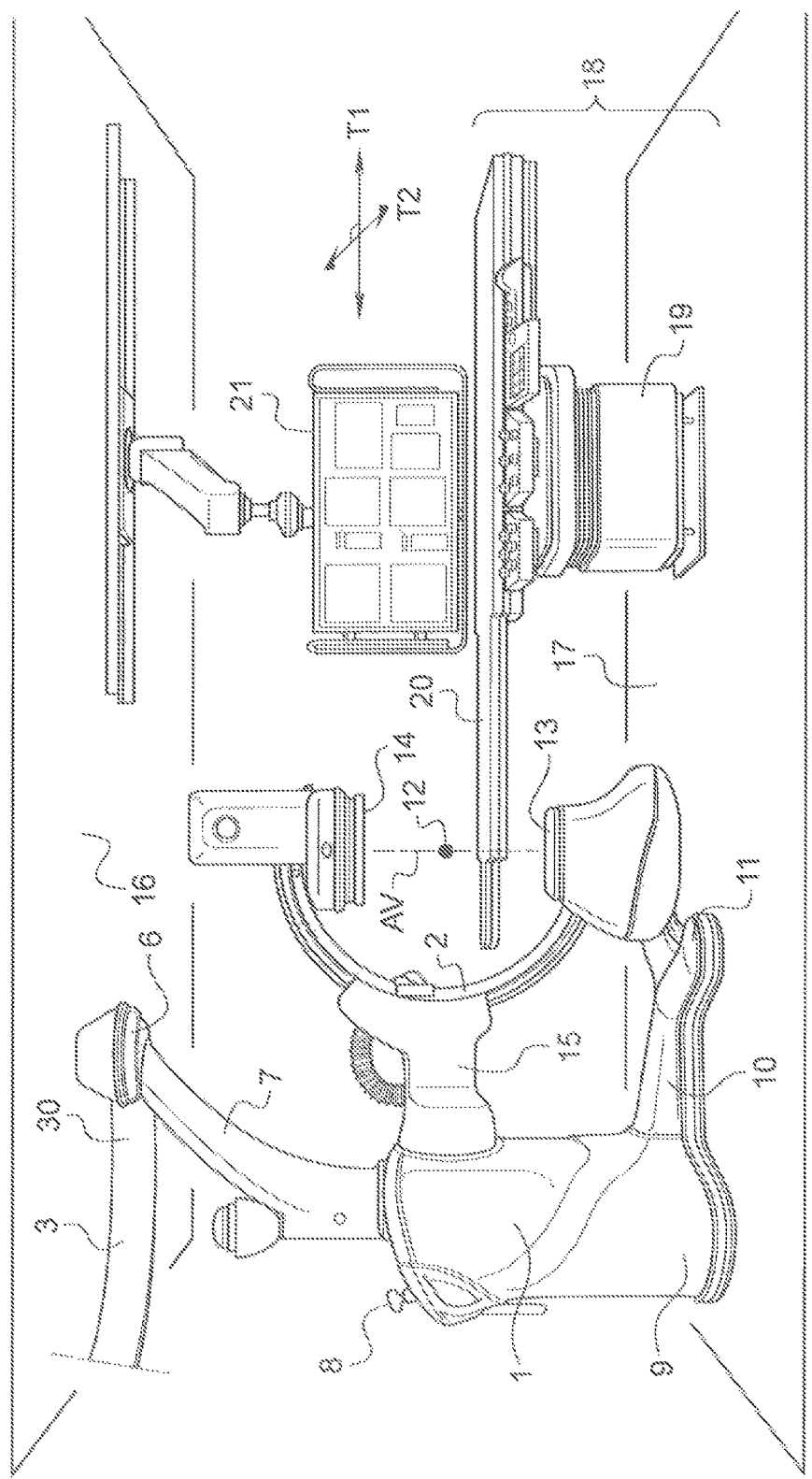
FIG. 2 shows an example of a mobile medical imaging robot according to at least one exemplary non-limiting embodiment, shown with an examination table in its neighborhood.

FIG. 2 shows an example of a mobile medical imaging robot according to at least one exemplary non-limiting embodiment, shown with an examination table in its neighborhood. An examination table 18 comprising a support 19 of a tray 20 is in position so that the C-arm 2 may take images of a patient who would lie on the tray 20. A screen 21 held on a rail fixed on the ceiling 16 may display some of the images taken by the C-arm 2.

A user can drive the motorized moving of the vehicle 1 by manipulating the joystick 8. A user may remove the robot from the examination table 18 with a translation T1 and then bring it again close to the examination table 18 again, by the reverse translation T1. By another translation T1 and or by a translation T2, user may center the C-arm on another part of the tray 20. User may also rotate vertically the robot around vertical axis AV, for example clockwise, so as to have better access to the tray 20 and to the patient who would lie on it, for example to perform some acts about this patient, and then rotate again vertically the robot around vertical axis AV, but this time counter-clockwise, so as to replace the robot in the imaging position.

Figure 3:
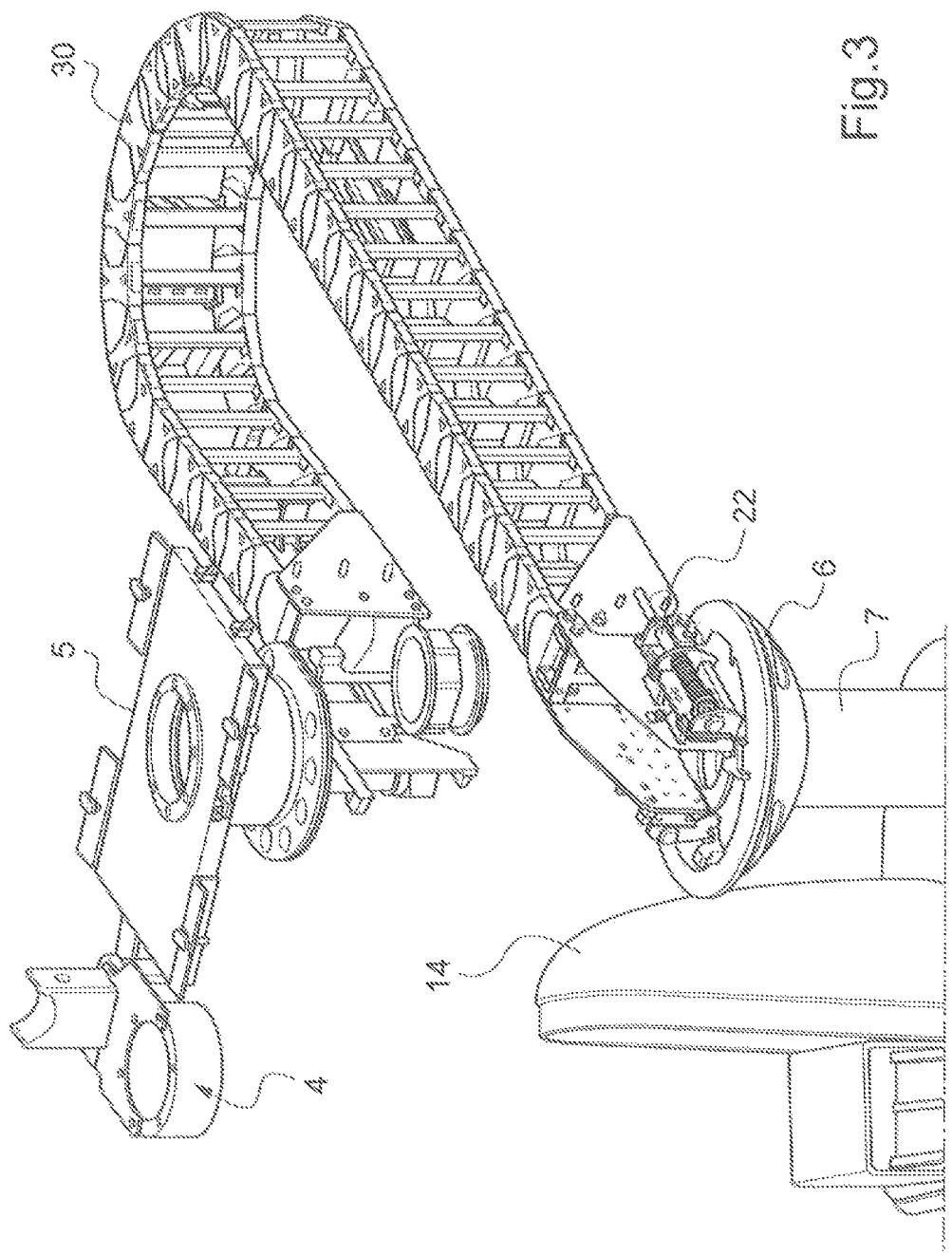
FIG. 3 shows an example of cable linking, to a ceiling of an examination room, an example of a mobile medical imaging robot according to at least one exemplary non-limiting embodiment.

FIG. 3 shows an example of cable linking, to a ceiling of an examination room, an example of a mobile medical imaging robot according to at least one exemplary non-limiting embodiment. At upper end of mast 7, one end of the cable chain 30 surrounding and protecting cable 3, is fixed to the saucer 6. Here the cable 3 is not visible within the cable chain 30. The saucer 6 allows for this end of the cable chain 30 to vertically rotate around upper end of mast 7. The other end of cable chain 30 is fixed to the pivot 5. The pivot 5 allows for this other end of the cable chain 30 to vertically rotate around the pivot 5. Just above the saucer 6, there is a security sensor 22 which is an anti over tensioning device, which means security sensor 22 detects an excessive tension of cable 3 before cable 3 itself or cable 3 connections become endangered.

Figure 4:
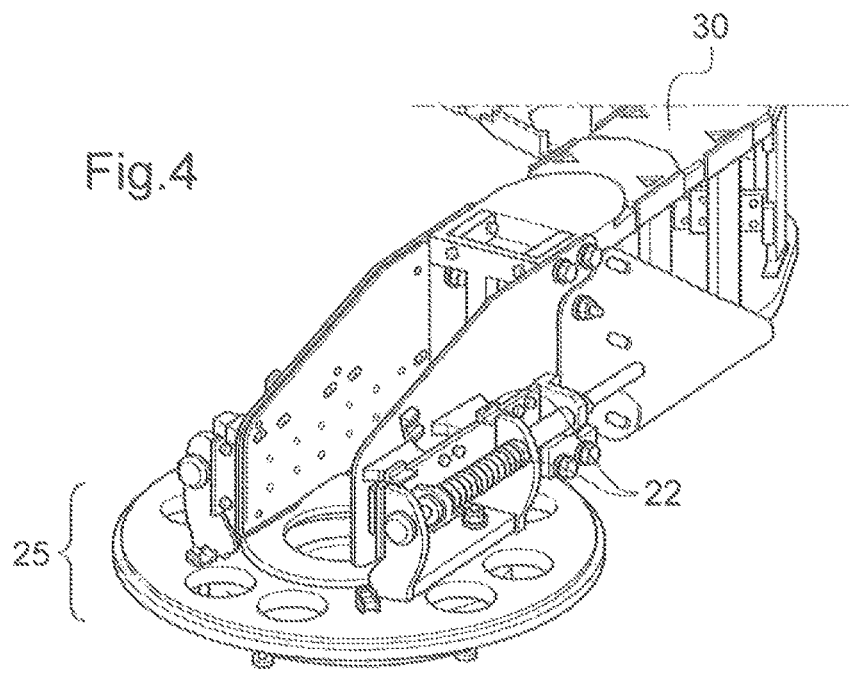
FIG. 4 shows a detail of FIG. 3, an example of an end of a cable linking, to a ceiling of an examination room, an example of a mobile medical imaging robot according to at least one exemplary non-limiting embodiment.

FIG. 4 shows a detail of FIG. 3, an example of an end of a cable linking, to a ceiling of an examination room, an example of a mobile medical imaging robot according to at least one exemplary non-limiting embodiment. A security sensor 22 detects whether there is an excessive tension of cable 3 before cable 3 itself or cable 3 connections become endangered, whereas another security sensor 25 detects whether there is an excessive vertical rotation in the same direction of the robot, to prevent entanglement of the cable 3 which could become harmful, if excessive, either for the cable 3 itself or for the cable 3 connections. Both security sensors 22 and 25 are located just above saucer 6, in the vicinity of one end of the cable chain 30.

Figure 5:
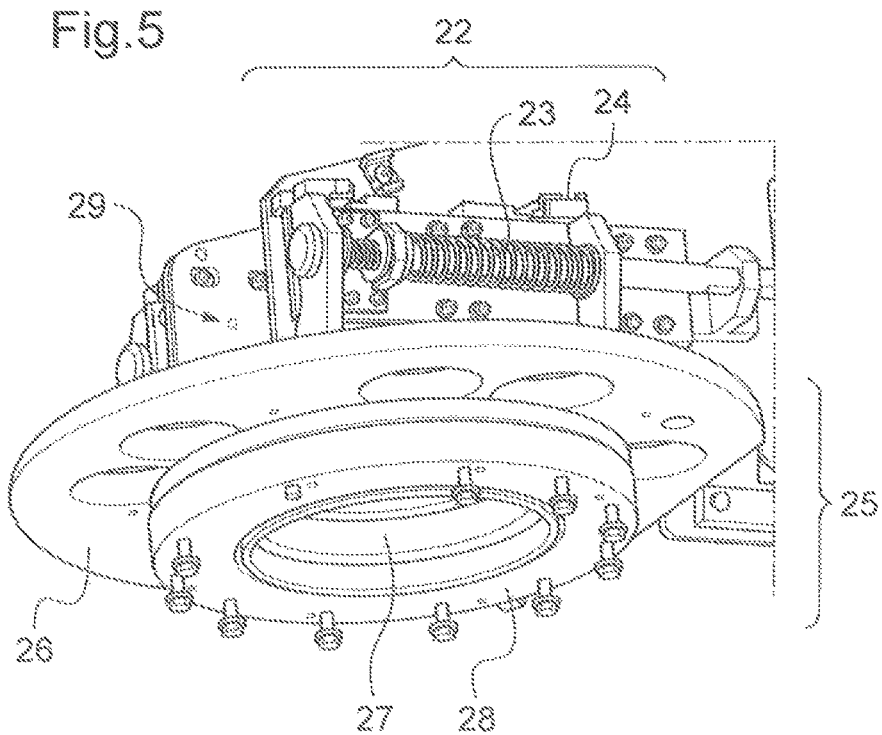
FIG. 5 shows a detail of FIG. 4, an example of security sensors located at an end of a cable linking, to a ceiling of an examination room, an example of a mobile medical imaging robot according to at least one exemplary non-limiting embodiment.

FIG. 5 shows a detail of FIG. 4, an example of security sensors located at an end of a cable linking, to a ceiling of an examination room, an example of a mobile medical imaging robot according to at least one exemplary non-limiting embodiment. Security sensor 22 detects an excessive tension of cable 3. Security sensor 22 mechanically detects such an excessive tension of cable 3. Indeed, security sensor 22 comprises one or more springs 23 which once compressed, because of an excessive tension of cable 3, trigger one or more switches 24 which in turn will trigger prevention of further cable 3 extension. So, security sensor 22, when detecting an excessive tension of cable 3, will lead to a blocking stopping any further extension of cable 3.

Security sensor 25 detects an excessive rotation of cable 3 in the same direction. Indeed, security sensor 25 comprises an encoder 29 which detects the angular rotation of a chain support 26 with respect to a ring 28 belonging to mast 7 via a ball bearing 27. Once this angular rotation exceeds a predetermined threshold, for example one full turn, or preferably half a turn, then further rotation in the same direction is prevented by a blocking. An alternative security sensor 25 to mechanically detect an excessive rotation of cable 3 in the same direction could be a mechanical rotation stop.

The written description uses exemplary non-limiting embodiments and examples to disclose the invention, including the best mode, and also to enable any person skilled in the art to practice the invention, including making and using any devices or systems and performing any incorporated methods. The patentable scope of the invention is defined by the claims, and may include other examples and embodiments that occur to those skilled in the art. Such other examples and embodiments are intended to be within the scope of the claims if they have structural elements that do not differ from the literal language of the claims, or if they include equivalent structural elements with insubstantial differences from the literal language of the claims.

What is claimed is:

1. A mobile medical imaging robot comprising:
   a medical imaging device;
   a motorized vehicle comprising at least one motor and configured to carry and move the medical imaging device along a surface;
   a cable configured to link the vehicle to the surface or a wall extending from the surface, wherein the cable is flexible and is disposed within and surrounded by a flexible chain; and
   a cable security system configured to detect when cable tension exceeds a predetermined acceptable value and prevent further movement of the motorized vehicle leading to still higher cable tension;
   wherein the motorized vehicle is driven manually by a user.

2. The mobile medical imaging robot of claim 1, wherein said motorized vehicle is driven by a user from a location away from where the mobile medical imaging robot is located.

3. The mobile medical imaging robot of claim 1, further comprising a human machine interface configured to perform said manual driving.

4. The mobile medical imaging robot of claim 3, wherein the human machine interface comprises an input device, said input device comprising one or more of a joystick, push-button, rotating knob, and track ball.

5. The mobile medical imaging robot of claim 4, wherein the human machine interface is configured to provide tactile feedback to the user.

6. The mobile medical imaging robot of claim 4, wherein the human machine interface is power assisted.

7. The mobile medical imaging robot of claim 4, wherein the human machine interface is configured so that input device movements generated by the user effectuate corresponding similar movements performed by the motorized vehicle.

8. The mobile medical imaging robot of claim 7, wherein the device movements comprise planar translational and/or rotational movements thereof which correspond to similar translational and/or rotational movements by the motorized vehicle.

9. The mobile medical imaging robot of claim 7, wherein a number of movements can be performed by said vehicle, wherein said number of movements include rotational movements about a vertical axis, and at least two translational movements orthogonal to each other.

10. The mobile medical imaging robot of claim 9, wherein the vertical axis contains the isocenter of the medical imaging device.

11. The mobile medical imaging robot of claim 1, wherein the cable transmits at least one of: power to the motorized vehicle, power to the medical imaging device, movement signals from the human machine interface, cooling for the medical imaging device, patient data, and imaging data from said medical imaging device.

12. The mobile medical imaging robot of claim 1, further comprising a rotation security system configured to detect vehicle rotation in a direction beyond a predetermined acceptable value and prevent further rotation of the vehicle in the direction.

13. The mobile medical imaging robot of claim 12, wherein the cable security system comprises a sensor configured to mechanically detect excessive cable tension and the rotation security system comprises a sensor configured to mechanically detect excessive rotation of the vehicle in any direction.

14. The mobile medical imaging robot of claim 1, wherein the medical imaging device is an x-ray c-arm.

15. The mobile medical imaging robot of claim 1, wherein the medical imaging device, under user control, is configured to move away from an examination table to allow access to a patient, and to move toward and about the examination table to a desirable location for taking images of the patient corresponding to an area of interest.

16. A mobile medical imaging robot comprising:
   a medical imaging device;
   a motorized vehicle comprising at least one motor and configured to carry and move the medical imaging device along a surface; and
   a cable configured to link the vehicle to a surface;
   at least one movement monitoring system comprising at least one sensor, said movement monitoring system configured to prevent any movement beyond a corresponding acceptable movement threshold; and
   a cable security system configured to detect when cable tension exceeds a predetermined acceptable value and prevent further movement of the motorized vehicle leading to still higher cable tension, wherein the cable is flexible and is disposed within a flexible chain;
   wherein the medical imaging device, under user control, is configured to move away from an examination table to allow access to a patient, and to move toward and about the examination table to a desirable location for taking images of the patient corresponding to an area of interest.

17. The mobile medical imaging robot of claim 16, wherein the medical imaging device comprises an x-ray c-arm.

* * * * *